(12) United States Patent
Rosoff et al.

(10) Patent No.: US 6,270,482 B1
(45) Date of Patent: Aug. 7, 2001

(54) MULTIPLE-DOSE SYRINGE

(75) Inventors: Jack P. Rosoff; Michael N. Hirsch, both of Portland; Ali S. Salem, Canby, all of OR (US)

(73) Assignee: Tri-Med International, LLC

( * ) Notice: Subject to any disclaimer, the term of this patent is extended or adjusted under 35 U.S.C. 154(b) by 0 days.

(21) Appl. No.: 09/392,870

(22) Filed: Sep. 9, 1999

(51) Int. Cl.$^7$ .................................................. A61M 5/24
(52) U.S. Cl. ................................... 604/200; 604/216
(58) Field of Search .............................. 604/200–207, 604/212, 214, 215, 216, 232

(56) References Cited

U.S. PATENT DOCUMENTS

| | | | |
|---|---|---|---|
| 3,892,237 | 7/1975 | Steiner | 128/216 |
| 5,281,198 | * 1/1994 | Haber et al. | 604/86 |
| 6,077,252 | * 6/2000 | Siegel | 604/214 |

* cited by examiner

*Primary Examiner*—Anhtuan T. Nguyen
*Assistant Examiner*—Ann Y Lam
(74) *Attorney, Agent, or Firm*—Brian A. Carpenter, Esq.; LeBoeuf, Lamb, Greene & MacRae, L.L.P.

(57) ABSTRACT

A multiple-dose syringe including a barrel with a closed end and an open end, the closed end having an injection port adapted to receive a needle. A plunger is slidably disposed through the open end of the barrel. A container is connected to an end of the plunger to move with the plunger. The container has a deformable shell with an opening at a forward end thereof and a predetermined quantity of fluid sealed therein by a closure member disposed over the opening. The container is slidably disposed in the barrel and includes a seal proximal to the forward end to form a first cavity in the barrel with a volume that is adjustable by moving the container in the barrel with the plunger so that fluid can be selectively drawn into and expelled from the first cavity. After at least a substantial portion of the fluid is expelled from the first cavity, the shell is configured to be collapsed by further pressure applied by the plunger to expel the predetermined quantity of fluid contained therein.

13 Claims, 3 Drawing Sheets

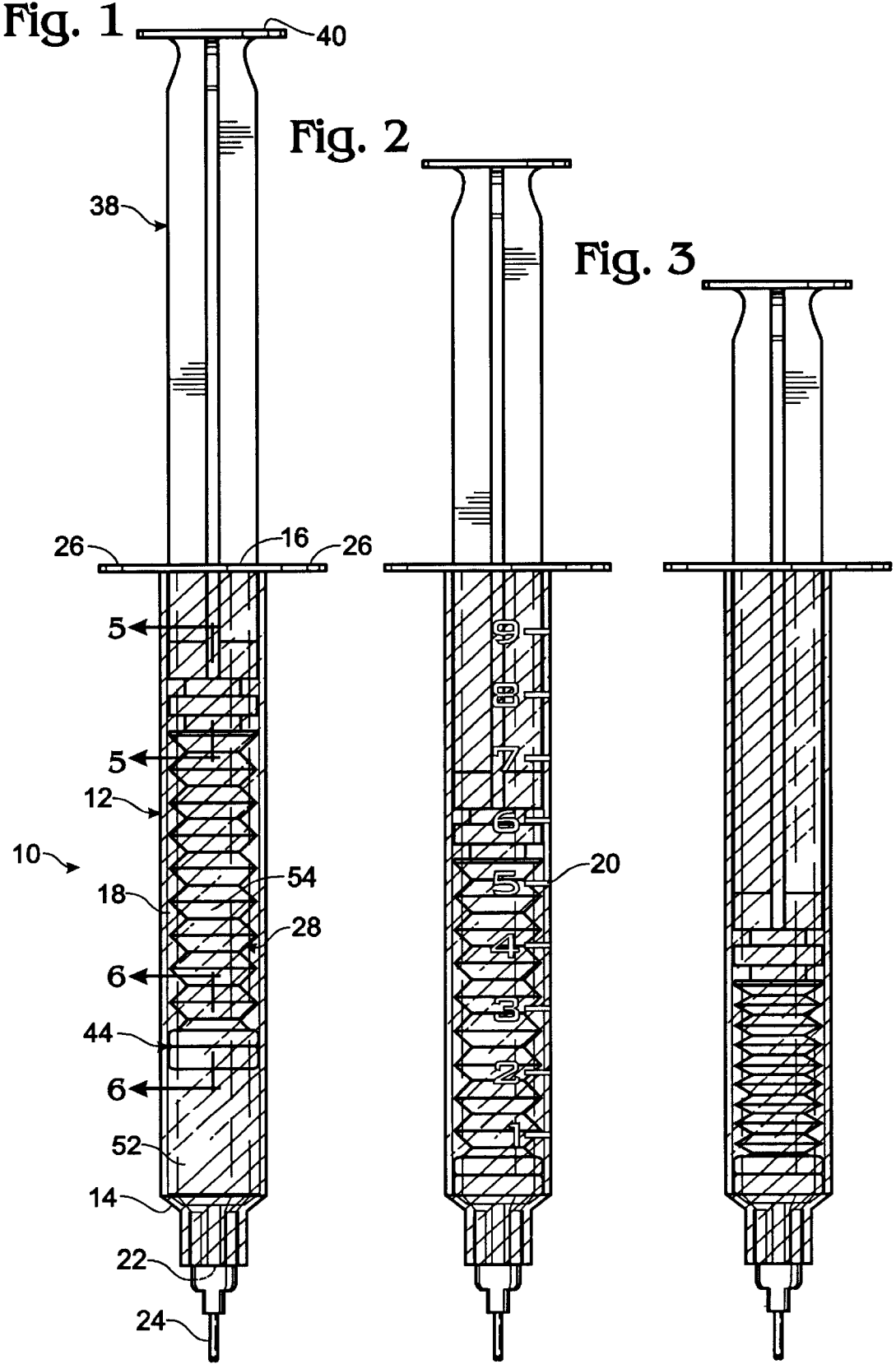

MULTIPLE-DOSE SYRINGE

FIELD OF THE INVENTION

The present invention relates to a syringe, and more particularly, to a syringe adapted to sequentially inject a plurality of fluids.

BACKGROUND OF THE INVENTION

When administering certain medications, it is sometimes necessary to inject sequentially two fluids into a patient. For example, during chemotherapy, small quantities of medicine are administered, usually through an IV. To insure that all of the medicine reaches the patient, the medication is followed by a saline flush. The saline flush rinses any residual medicant through the IV and into the patient. Traditionally, the saline flush is administered as a separate step from the medicine. In particular, a standard single-dose syringe is used to deliver the medicine. A health care worker then reloads the syringe with the desired quantity of saline. The saline is then injected into the IV to flush the medicine into the patient. This process is time consuming, and, because it requires multiple operations with the needle, it increases the chances health care workers will inadvertently prick themselves with the needle.

Various types of syringes for dispensing sequentially multiple fluid doses have been proposed to address the above problem. For example, U.S. Pat. No. 4,702,737 to Pizzino discloses a multiple-dose, single-barrel syringe utilizing a plurality of telescoping sections of progressively decreasing diameter. Unfortunately, the design of this syringe requires that all of its chambers be pre-loaded with fluids at the time of manufacture. In particular, the syringe incorporates a needle that extends into the barrel of the syringe to puncture a membrane to release the second fluid. The internal needle prevents the syringe from being completely closed to draw fluid into the barrel. As a result of the need to completely preload the syringe, it is necessary to stock separate syringes for each medication. Such medications are often expensive and have limited shelf life, thereby limiting the usefulness of this design.

U.S. Pat. Nos. 4,439,184, 4,715,854, and 5,720,731 to Wheeler, Viallancourt and Armata, respectively, disclose multiple-dose syringes with two pistons and a bypass zone. In each of these patents, a second chamber between the first and second pistons is filled and dispensed through the bypass zone, which is located on one side of the barrel wall near the injection port. Syringes with a bypass zone and multiple pistons are complicated to manufacture and require many specially designed parts. In most of the floating piston designs, the syringe must be preloaded with both fluids because the syringe cannot draw fluids or aspirate. In addition, the floating piston is subject to jamming and may thereby become difficult to depress.

BRIEF DESCRIPTION OF THE DRAWINGS

FIG. 1 is a side view of a syringe constructed according to the present invention.

FIG. 2 is a side view of the syringe of FIG. 1 with the fluid in a first cavity expelled.

FIG. 3 is a side view of the syringe of FIG. 1 with part of the fluid in a container expelled.

DETAILED DESCRIPTION OF THE PREFERRED EMBODIMENTS

Figure 4:
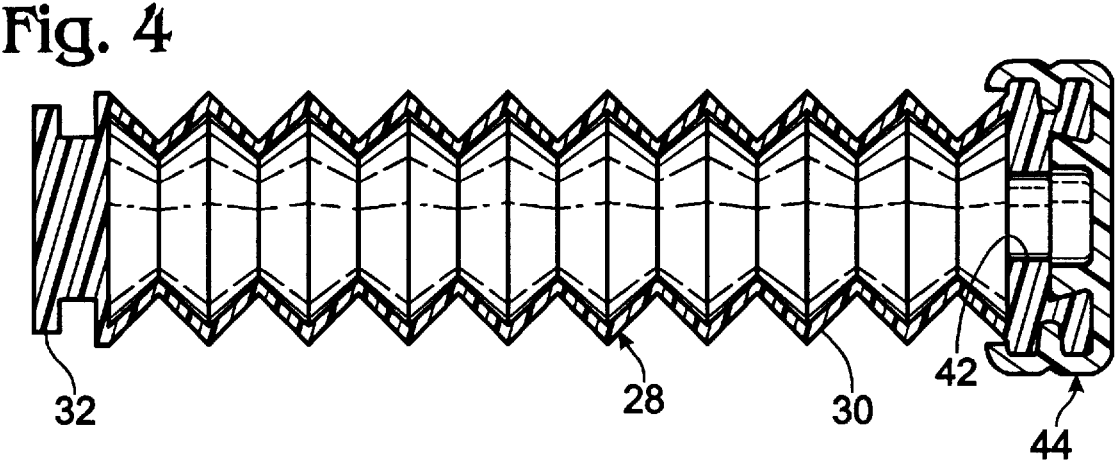
FIG. 4 is a sectional view of a container constructed according to the present invention.

A syringe constructed according to the present invention is shown generally at 10 in FIG. 1. Syringe 10 includes a cylindrical hollow barrel 12 with a closed end 14 and an open end 16. The cylindrical walls of the barrel define a cavity 18, which is adapted to receive and hold the fluid to be dispensed. The cavity typically has a volume or capacity of between 1 and 10 cc, and is marked with gradations 20 to permit the amount of fluid to be measured. It should, or course, be understood, that the present invention could be implemented with syringes of any size. The closed end has an injection port 22 which is configured to receive a needle 24. Finger grips 26 are disposed adjacent to the open end of the barrel and allow the user to grasp the barrel when drawing fluids into or dispensing fluids out of the syringe.

A fluid container 28 is slidably received into barrel 12 through open end 16. As shown in FIG. 4, the container includes a cylindrical bellows-like shell 30. The shell is preferably made of a flexible material that is non-reactive to the fluid stored therein. For instance, polypropylene is a suitable material when the container is used to hold saline. The flexible material allows the container to collapse to dispense fluid, as described in more detail below and illustrated in FIG. 3. It should be understood that other collapsible configurations besides a pleated or bellows structure could be used for shell 30.

Figure 5:
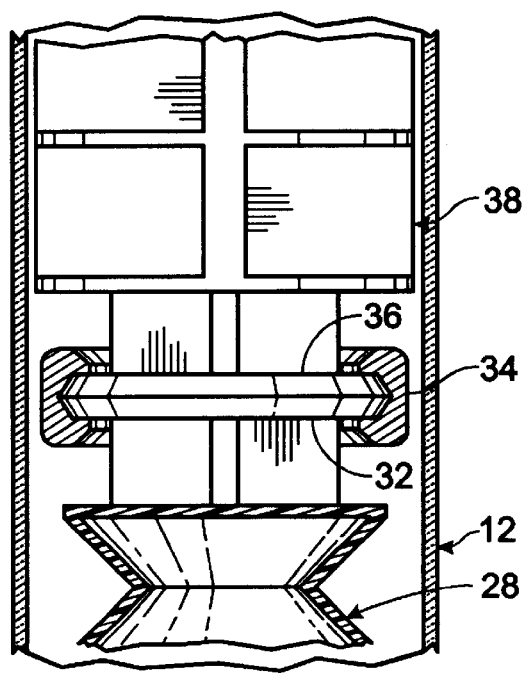
FIG. 5 is an enlarged view of a coupler configured to connect a plunger to the container of FIG. 4.

As shown in FIG. 5, a connector 32 is formed on a closed end of the shell. Connector 32 is joined by a coupler 34 to corresponding a connector 36 formed on the end of a plunger 38. Plunger 38 has an elongate shaft extending from connector 36 to a thumb pad 40, which shown in FIG. 1 and is used to depress or retract the plunger. Coupler 34 is preferably formed of a butyl rubber compound and deforms to slip over the connectors. The connection between the container and the plunger allows the plunger to be used to move the container up and down in the barrel. As such, many other connections between the container and the plunger could also be used, including, for instance, glue or clips. Also, the plunger could be formed integrally with the container.

Figure 6:
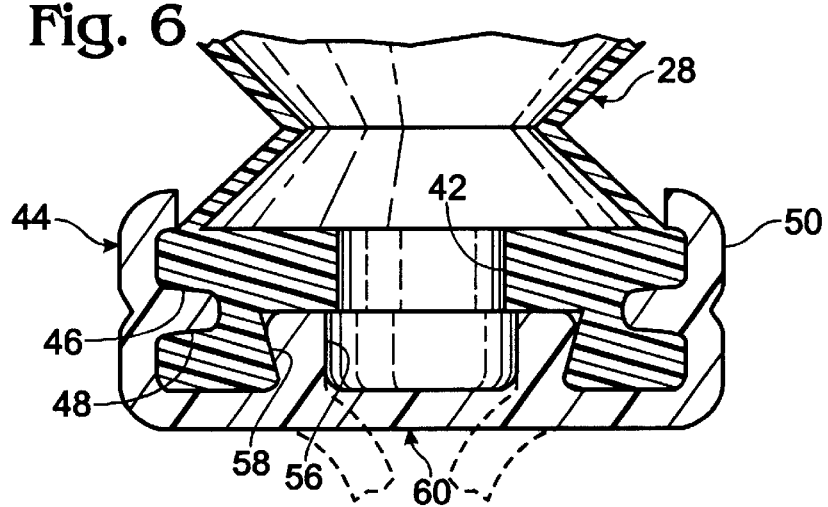
FIG. 6 is a sectional view of a container cap constructed according to the present invention.

The end of the shell opposite connector 32 includes a passage 42 that is selectively sealed by a closure member in the form of a cap 44, as shown in FIG. 6. The shell includes a circumferential groove 46 that receives a corresponding flange 48 formed on the inside surface of the cap. The cap is preferably formed of a butyl rubber compound to allow it be fit over the end of the shell and retained thereon. The outer perimeter of the cap is shaped to form a perimeter seal 50 and sized to fit snuggly within the barrel, similar to the tip on a standard plunger. When the container is placed in the barrel, as shown in FIGS. 1–3, the perimeter seal effectively separates the barrel into two regions or cavities: a first region 52 disposed between the closed end and the cap and a second region 54 disposed behind the cap and occupied by the container.

An inwardly facing cup 56 is formed on the end face of the cap. The walls of the cup are received in a recess 58 formed in the end of the shell proximal to passage 42. A slight outward tilt to the walls of the cup and recess serves to help retain the cap on the end of the shell. In particular, any pressure created in the fluid in the shell tends to urge the walls of the cup outward to tighten the seal between the cap and shell, thereby preventing the escape of fluid and preventing the cap from being pushed off the end of the shell.

The bottom of the cup forms a rupture zone 60 that is pressure rupturable, i.e. ruptures when fluid pressure across the rupture zone exceeds some desired level. For instance, the thickness of the rupture zone may be varied to control the pressure at which occurs. Alternatively, a defect may be created in the rupture zone to provide a predetermined failure location. For example, the defect can be a cut extending part way through the material of the cap or a series of partial perforations. In general, however, the rupture zone should fail at a relatively predictable pressure. Furthermore, the pressure should be readily achievable by finger pressure on the thumb pad of the plunger. It should be noted that any pressure created in the shell is matched by backpressure of the fluid in the first region. Therefore, zone 60 will not rupture until the fluid in the first region is substantially completely expelled. The dashed lines in FIG. 6 depict the rupture zone after rupture.

Figure 7:
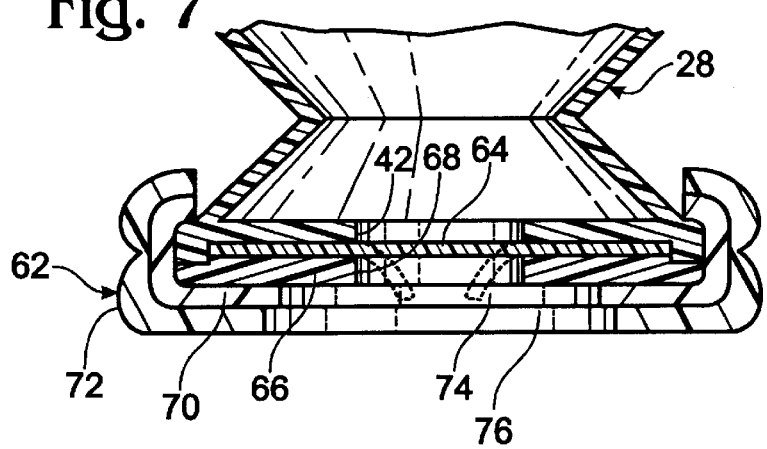
FIG. 7 is an alternative embodiment of the cap of FIG. 6.

An alternative cap structure 62 is shown in FIG. 7 and includes a rupture sheet 64 disposed over passage 42. The rupture sheet is preferably formed of a thin sheet of rubber, plastic or non-corrosive metal. The rupture sheet is supported and retained against the end of the shell by a seal flange 66 with a central aperture 68 aligned with passage 42. The aperture allows fluid to pass after rupture of the sheet. The seal flange is held in place on the end of the shell by a clamp ring 70 that is crimped over the end of the shell. The clamp ring is preferably formed from a thin deformable cylinder of metal, such as used on the end of a medicine vial. A seal 72, preferably formed of a butyl rubber compound, is disposed over the clamp ring to form a seal with the walls of the barrel, as previously described. The clamp ring and seal include apertures 74 and 76, respectively, that allow fluid from the container to pass after the sheet is ruptured, as shown by the dashed lines in FIG. 6.

As described above, the syringe of the present invention is preferably pre-loaded or filled with saline or other second fluid at the time of manufacture. The plunger is also attached to the container and the resulting assembly is packaged in a sterile condition for shipment. The needle may or may not be attached, depending on the configuration desired. It should be noted that the barrel and plunger of the present invention are preferably unmodified components from a standard syringe design. This eliminates the need to create new and specialized parts for use with a two-fluid syringe. Although it is preferred that the container be pre-loaded in the syringe, it should also be understood that the container could be provided as a separate unit for installation and use with an otherwise standard syringe. This variation is facilitated by use of a design that incorporates unmodified parts from a standard syringe.

Figure 8:
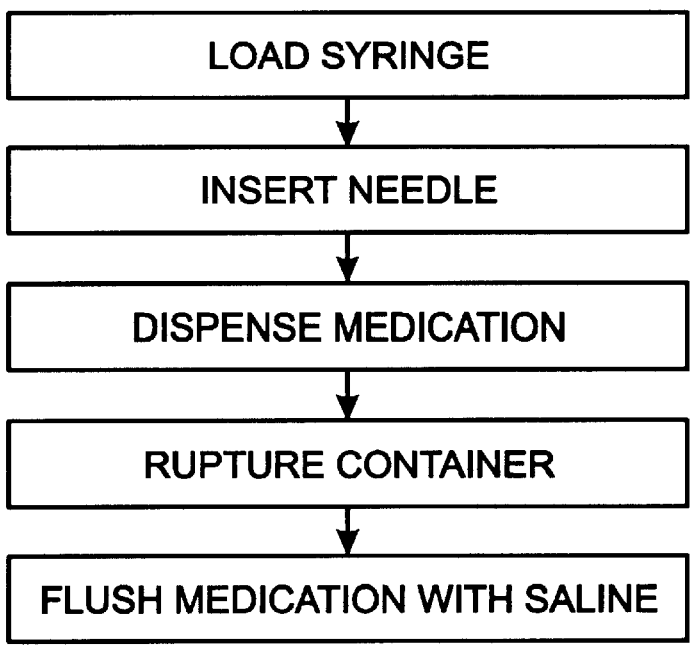
FIG. 8 is a block diagram of the steps involved in utilizing the syringe of FIG. 1.

FIG. 8 depicts the steps involved in using a syringe according to the present invention. First, the operator selects a pre-loaded syringe package and removes the sterile envelope. If necessary, a needle is attached to the barrel. The operator then loads the desired amount of medicine into the syringe similar to loading a conventional syringe. This is possible because the plunger/container functions like a standard plunger until the medicine in the forward region is expelled and the container is ruptured. Thus, the operator can retract the plunger to load air into the syringe, insert the needle into a medicine vial, push forward on the plunger to inject the air into the vial and then retract the plunger again to withdraw the desired amount of medicine. The needle is then inserted into an IV, and the medicine is dispensed by depressing the plunger, as shown by comparison of FIGS. 1 and 2. When the medicine is dispensed, subsequent pressure on the plunger ruptures the cap, releasing the saline or other fluid in the container. The plunger is then further depressed to compress the container, as depicted in FIG. 3, and force the secondary fluid out, thereby flushing the medicine.

It can be seen that the syringe of the present invention provides an economical and easy to use solution to the problem of sequentially injecting two fluids. The simple operation saves time and decreases the chances that a health care worker will inadvertently stick themselves with the needle.

While the invention has been disclosed in its preferred form, the specific embodiments thereof as disclosed and illustrated herein are not to be considered in a limiting sense as numerous variations are possible. Applicant regards the subject matter of the invention to include all novel and non-obvious combinations and subcombinations of the various elements, features, functions and/or properties disclosed herein. No single feature, function, element or property of the disclosed embodiments is essential. The following claims define certain combinations and subcombinations which are regarded as novel and non-obvious. Other combinations and subcombinations of features, functions, elements and/or properties may be claimed through amendment of the present claims or presentation of new claims in this or a related application. Such claims, whether they are different, broader, narrower or equal in scope to the original claims, are also regarded as included within the subject matter of applicant's invention.

We claim:

1. A multiple-dose syringe, comprising:
   a barrel having a closed end and an open end, the closed end having an injection port adapted to receive a needle;
   a plunger slidably disposed through the open end of the barrel; and
   a container connected to an end of the plunger to move with the plunger, the container having a deformable shell with an opening at a forward end thereof and having a predetermined quantity of fluid sealed therein by a closure member disposed over the opening, wherein the container is slidably disposed in the barrel and includes a seal proximal to the forward end to form a first cavity in the barrel with a volume that is adjustable by moving the container in the barrel with the plunger so that fluid can be selectively drawn into and expelled from the first cavity, and where, upon expelling at least a substantial portion of the fluid from the first cavity, the shell is configured to be collapsed by further pressure applied by the plunger to expel the predetermined quantity of fluid contained therein.

2. The syringe of claim 1, wherein the closure member includes a rupture zone separating the fluids in the first chamber and the container and further wherein the rupture zone is configured to rupture when a user presses down on the plunger with a predetermined force after at least a substantial portion of the fluid in the first cavity has been expelled.

3. The syringe of claim 1, wherein the container includes a closed rear end wall opposite the opening and further comprising a coupler disposed between the plunger and the rear end wall to connect the plunger to the container.

4. The syringe of claim 3, wherein the container has a pleated shell.

5. The syringe of claim 1, wherein the closure member is integrally formed with the seal.

6. The syringe of claim 1, wherein the closure member includes a rupture sheet disposed over the opening and configured to rupture to allow fluid in the container to be expelled.

7. The syringe of claim 6, wherein the closure member is configured to rupture when pressure is applied to the plunger after substantially all of the fluid in the first cavity is expelled.

8. The syringe of claim 1, wherein the shell is formed generally in the shape of a bellows.

9. The syringe of claim 1, wherein the container includes a connector adapted to be coupled to a corresponding connector formed on an end of the plunger.

10. The syringe of claim 1, wherein the container is filled with saline.

11. The syringe of claim 10, wherein the first chamber can be emptied without damaging the closure member.

12. A multiple-dose syringe, comprising:
   a barrel having first and second cavities and an injection port;
   a plunger slidably disposed in the barrel; and
   a pressure-rupturable fluid-tight member separating the first and second cavities, where the member is configured to rupture when a user presses down on the plunger with a predetermined force, wherein the pressure-rupturable fluid-tight member is attached to a container disposed in the second cavity, the container having a deformable shell that is configured to be collapsed by pressure applied by the plunger.

13. A multiple-dose syringe, comprising:
   a barrel having first and second cavities and an injection port;
   a plunger slidably disposed in the barrel; and
   a pressure-rupturable fluid-tight member separating the first and second cavities, where the member is configured to rupture when a user presses down on the plunger with a predetermined force, wherein the pressure-rupturable fluid-tight member is attached to a container disposed in the second cavity, the container having a deformable pleated shell that is configured to be collapsed by pressure applied by the plunger.

* * * * *